United States Patent
Bratslavsky et al.

(10) Patent No.: US 6,811,312 B2
(45) Date of Patent: Nov. 2, 2004

(54) DENTAL X-RAY POSITIONING USING ADHESIVES

(75) Inventors: Aaron Bratslavsky, New York, NY (US); Arkadiy Royzen, New York, NY (US); Stan Mandlekern, New York, NY (US)

(73) Assignee: Schick Technologies, Inc., Long Island City, NY (US)

( * ) Notice: Subject to any disclaimer, the term of this patent is extended or adjusted under 35 U.S.C. 154(b) by 0 days.

(21) Appl. No.: 10/067,753

(22) Filed: Feb. 8, 2002

(65) Prior Publication Data

US 2003/0152196 A1 Aug. 14, 2003

(51) Int. Cl.⁷ .................................................. A61B 6/14
(52) U.S. Cl. ........................ 378/191; 378/168; 378/170
(58) Field of Search ................ 378/98.8, 168, 378/169, 170, 191

(56) References Cited

U.S. PATENT DOCUMENTS

| | | | |
|---|---|---|---|
| 4,197,855 A | 4/1980 | Lewin | 128/653 |
| 4,866,750 A | 9/1989 | Chavarria et al. | 378/168 |
| 4,912,740 A | 3/1990 | Liese, Jr. | 378/169 |
| 5,001,738 A * | 3/1991 | Brooks | 378/170 |
| 5,044,008 A | 8/1991 | Jackson | 378/168 |
| 5,450,465 A * | 9/1995 | Tanaka | 378/168 |
| 5,652,779 A | 7/1997 | Levy et al. | 378/170 |
| 5,667,537 A | 9/1997 | Richiardone et al. | 29/623.2 |
| 5,995,583 A | 11/1999 | Schick et al. | 378/38 |
| 6,062,730 A | 5/2000 | Sims et al. | 378/168 |
| 6,212,435 B1 | 4/2001 | Lattner et al. | 607/134 |
| 6,216,870 B1 * | 4/2001 | Welp | 206/454 |
| 6,315,444 B1 * | 11/2001 | Koren | 378/169 |
| 6,320,934 B1 * | 11/2001 | Carroll et al. | 378/98.8 |
| 6,382,831 B1 * | 5/2002 | Bacchetta et al. | 378/170 |

* cited by examiner

*Primary Examiner*—David V. Bruce
*Assistant Examiner*—Allen C. Ho
(74) *Attorney, Agent, or Firm*—Fitzpatrick, Cella, Harper & Scinto

(57) ABSTRACT

A system for dental x-ray examinations includes an image receptor, and a holder removably bonded to the image receptor by an adhesive coating. The system for dental x-ray examinations provides the clinician with a greater freedom of positioning and thereby improves upon the effectiveness of x-ray examinations, as well as upon patient comfort.

22 Claims, 6 Drawing Sheets

DENTAL X-RAY POSITIONING USING ADHESIVES

BACKGROUND OF THE INVENTION

1. Field of the Invention

This invention relates generally to the field of dental positioning systems for electronic and film x-ray examinations, and more particularly to a dental positioning system for positioning and aligning dental films and electronic x-rays sensors using adhesives.

2. Related Art

Intra-oral x-rays are an important aspect of dental care. Such x-rays have many uses, including diagnosing cavities and lesions, documenting treatment, and assisting in guiding procedures, among other things. Radiographs obtained using x-rays may be taken using either x-ray sensitive film or an x-ray sensitive electronic image sensor, such as a digital image sensor, as the image receptor. In either case, the receptor must be placed in the mouth and carefully aligned such that the x-rays emanating from the x-ray source are incident upon it. For example, in many applications it is desirable for the receptor to be positioned such that it is perpendicular to the x-ray beam. In any event, if the receptor is not placed and aligned correctly in the patient's mouth, clinically usable images generally may not be obtained.

Because of the need for accurate positioning, and because of the inherent difficulties involved, several devices have been proposed to assist dental practitioners in placing and aligning the receptor. Speaking generally, such devices are designed to grip the receptor and to have a bite area such that when the patient engages his or her teeth on the device, the device attempts to urge the receptor into the proper position. Some devices also have attachments which protrude from the mouth and give the practitioner an alignment point so that he or she can properly position the x-ray source.

In the specific case of digital radiology, a solid state image sensor (such as, for example, an image sensor comprising a charge-coupled device (CCD) or a CMOS active pixel sensor array (APS)) is used in place of film. Such sensors are typically 5–6 mm thick, and often have a cable which delivers the image from the sensor to a processing unit, such as a computer. The positioning devices used for such electronic sensors should grip the sensors quite firmly in order to ensure that they are not moved out of position by the tension on the cable. Moreover, electronic sensors, unlike pieces of film, are re-usable, and therefore should preferably be covered by a sterile infection barrier, such as a sheath. As a result, the conventional devices used to position electronic sensors tend to mechanically grip the sensor around its edges.

Although prior art techniques are generally good for their intended purposes, there are several problems with existing dental x-ray positioning systems, with respect to both film and electronic receptors, which are not addressed adequately by these techniques. One problem is that the gripping device presents distinct protrusions around the edges of the receptor. These protrusions can be quite uncomfortable to the patient and may even injure the patient if they become sharp.

Another problem is that the existing holder systems present a fixed relationship between the receptor and the bite area, thereby allowing very little flexibility of placement. That is, because the anatomy of the mouth varies between patients, the user has very little flexibility in how the receptor will be positioned relative to the teeth being imaged. This is a significant drawback, since it may be difficult or impossible to achieve a useful image without some flexibility in the positioner. This may lead not only to sub-optimal coverage of dental anatomy, but also to patient discomfort, due to the presence of sharp edges in film packaging or by the lack of degrees of freedom provided by the holders. Prior attempts to improve upon patient comfort included providing a cushioned package. Some examples of a cushioned system include U.S. Pat. No. 4,912,740 to Liese, Jr.; U.S. Pat. No. 5,044,008 to Jackson; and U.S. Pat. No. 6,062,730 to Sims et al. Such systems, however, resulted in only limited improvements because even if the device is soft, if it is forced into position, it can nonetheless be uncomfortable to the patient.

U.S. Pat. No. 4,866,750 to Chavarria discusses an image receptor holder on a multi-dimension stage. The device allows for horizontal and vertical movement of the image receptor with respect to the x-ray source, so that the device may be adjusted somewhat to accommodate the contours of a particular patient's mouth. However, while this system may in theory allow some flexibility in placement, it is impracticable to utilize it in a clinical environment due to its large and bulky structure, which can make it difficult to adjust the device as needed.

Another problem is that receptors may vary in dimension, either due to manufacturing variations or due to the existence of various sizes of receptors. Film, for example, is available in size 2 (bitewing), size 1 (anterior) and size 0 (pediatric), among other sizes, and many electronic sensors are available in corresponding sizes. Because of these variations, a unique gripping device should be used for each exact size of sensor, which introduces additional complications to the process.

Another problem is that the gripping devices will fatigue if used repeatedly, thereby limiting their useful life.

One problem specific to electronic sensors is that because the gripping device should make very tight contact with the sensor, the sterile sheath may be torn, thus contaminating the sensor or even damaging the sensor itself through mechanical fatigue. This is highly problematic, as an electronic sensor is a relatively costly item, typically on the order of several thousands of dollars.

There is a need, therefore, for an x-ray positioning system that departs significantly from the conventional methodologies, takes an entirely fresh approach towards solving the problems discussed above, and provides a simple and effective way of positioning and aligning both film and electronic sensors.

SUMMARY OF THE INVENTION

Accordingly, it is an object of this invention to provide a dental x-ray positioning system which overcomes the above-mentioned problems. More specifically, it is an object of this invention to provide a positioning system wherein the positioning device connects to the receptor by attaching to an adhesive coating. In this way, the receptor is bonded to a holder in a convenient location and orientation. The adhesive coating may be on the positioning device or on the receptor.

It is also an object of this invention to provide a novel holder system for positioning and aligning dental x-ray films or sensors. The system uses an adhesive to bond the holder to an encapsulated film or sensor.

It is also an object of this invention to provide a positioning system wherein there are no uncomfortable holding tabs, protrusions, or protruding edges associated with the receptor.

It is also an object of this invention to provide a positioning system wherein the positioning device or positioner may be attached to the receptor at any point along the surface, thereby maximizing positioning flexibility.

It is also an object of this invention to provide a positioning system wherein the positioning device and the receptor are removably attached to each other by the adhesive.

It is also an object of this invention to provide a positioning system wherein the same positioner may be used with receptors of any dimension.

It is also an object of this invention to provide the clinician with a greater freedom of positioning to improve upon patient comfort.

A system for dental x-ray examinations according to one embodiment of this invention comprises an image receptor and a holder removably bonded to the image receptor by an adhesive coating on a surface of the holder. The image receptor may comprise film or an electronic sensor. If the image receptor is an electronic sensor, the electronic sensor may comprise a CMOS active pixel sensor array or a charge-coupled device.

Another embodiment of this invention provides a holder for a dental image receptor having an adhesive coating to removably bond the holder to the dental image receptor.

A system for dental x-ray examinations according to one embodiment of this invention comprises an image sensor, a sheath covering the image sensor, and a holder having an adhesive coating and bonded to the sheath by the adhesive coating. The holder may be bonded to the sheath at any point along a surface of the image sensor.

The image sensor may comprise a charge-coupled device or a CMOS active pixel sensor array. The sheath may be a material selected from the group comprising paper, cotton, sponge, rubber, plastic, latex, and nylon. The adhesive may be selected from the group comprising tape, epoxy, hot melt, and sealant.

A system for dental x-ray examinations according to another embodiment of this invention comprises an image sensor, a sheath covering the image sensor, an adhesive coating on the sheath, and a holder bonded to the sheath by the adhesive coating.

BRIEF DESCRIPTION OF THE DRAWINGS

The invention will be more clearly understood by reference to the following detailed description of exemplary embodiments in conjunction with the accompanying drawings, in which.

DETAILED DESCRIPTION OF THE INVENTION

As described briefly above, this invention is a dental positioning system for positioning and aligning dental x-ray films or sensors using adhesives. In one embodiment, the invention provides a positioning device which connects to the receptor by way of an adhesive.

Figure 1:
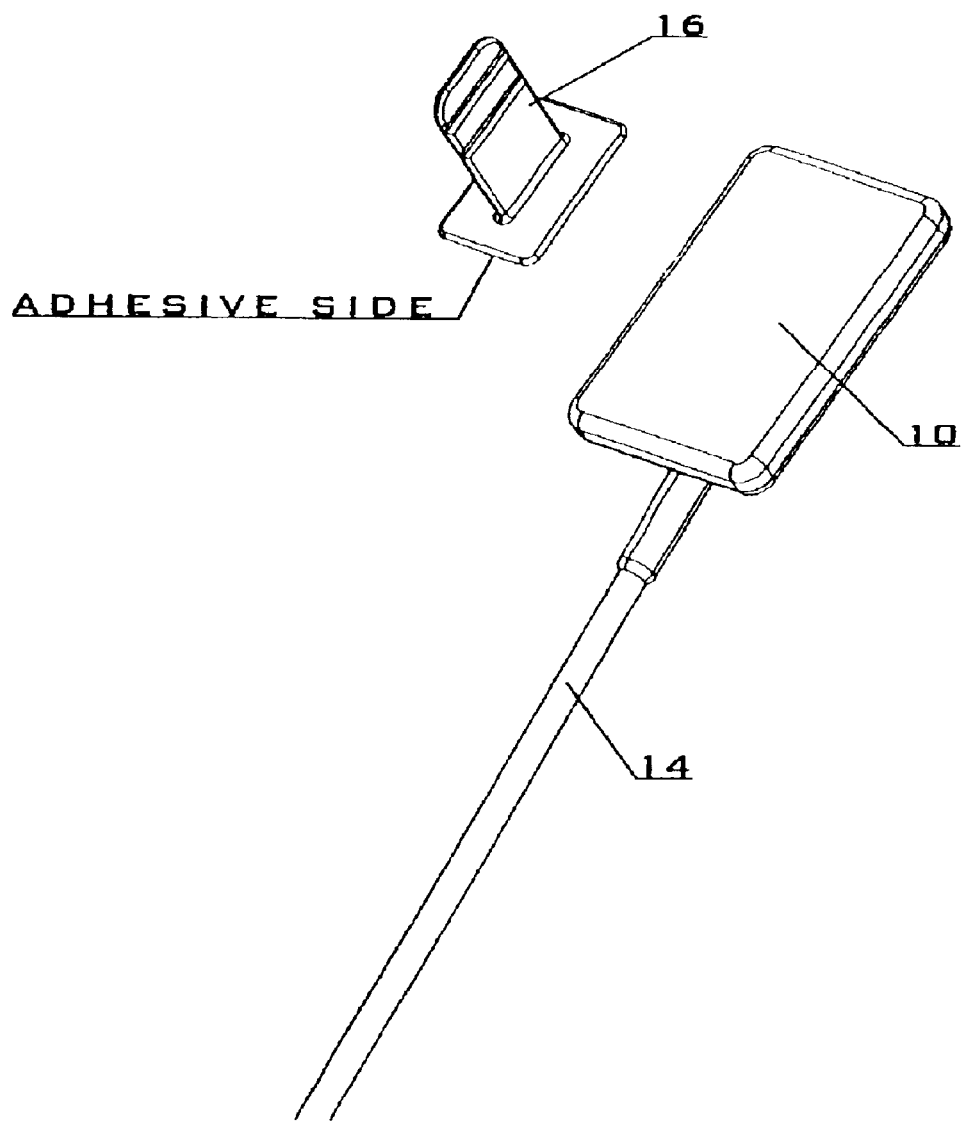
FIG. 1 is an illustration of the positioning system before being assembled according to one embodiment of the present invention.

FIG. 1 shows the dental positioning system according to one embodiment of the present invention. An electronic sensor 10 is shown in FIG. 1. A cable 14 protrudes from the sensor 10 to deliver the image to a processing unit (not shown). Also shown is a holder 16 on which a pressure sensitive adhesive is applied. The adhesive may be applied either in the manufacturing process or by the user, such as by the dental practitioner or his assistant. The sensor 10 is bonded with the adhesive to the holder 16 in a desired location. It is noted that although the adhesive is applied to the holder in the embodiment shown in FIG. 1, as is the preferred embodiment, the present invention is of course not limited to this embodiment, and various modifications may be imagined. For example, the adhesive could be applied to the sensor.

Figure 2:
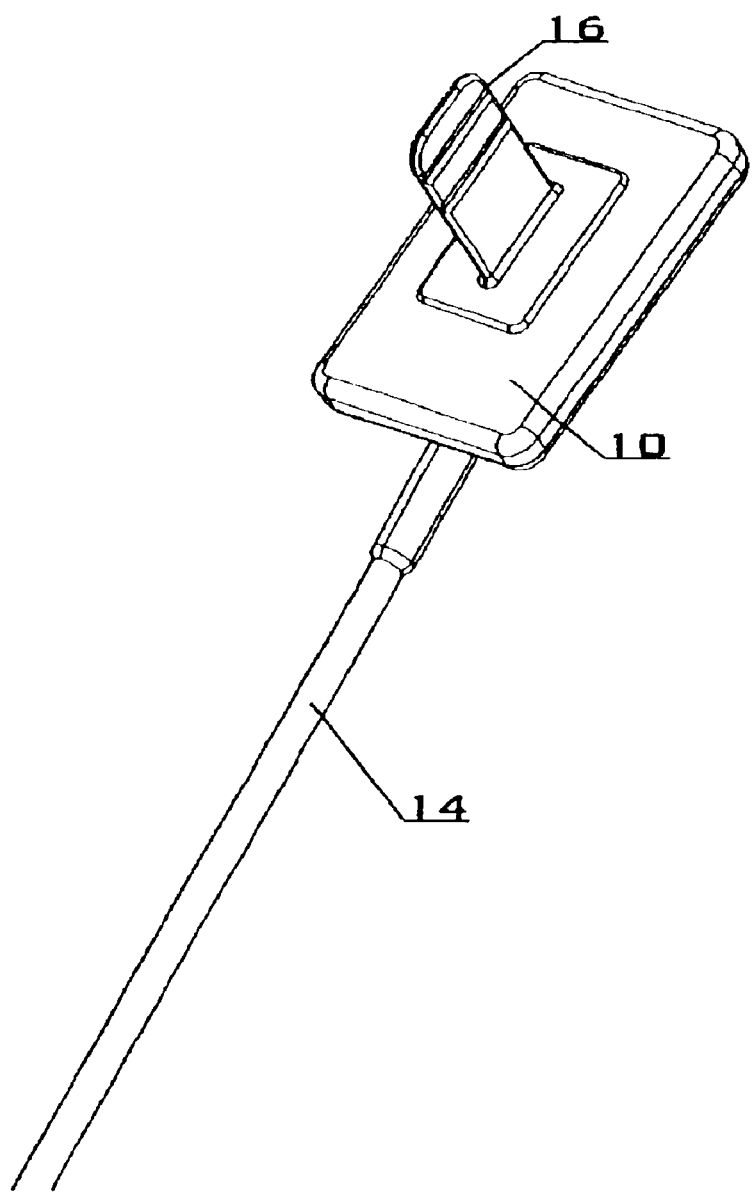
FIG. 2 is an illustration of the positioning system after being assembled according to the embodiment shown in FIG. 1.

FIG. 2 is an illustration of the positioning system after being assembled according to the embodiment shown in FIG. 1. FIG. 2 shows the receptor 10, with the holder 16 affixed by way of the adhesive.

Figure 3:
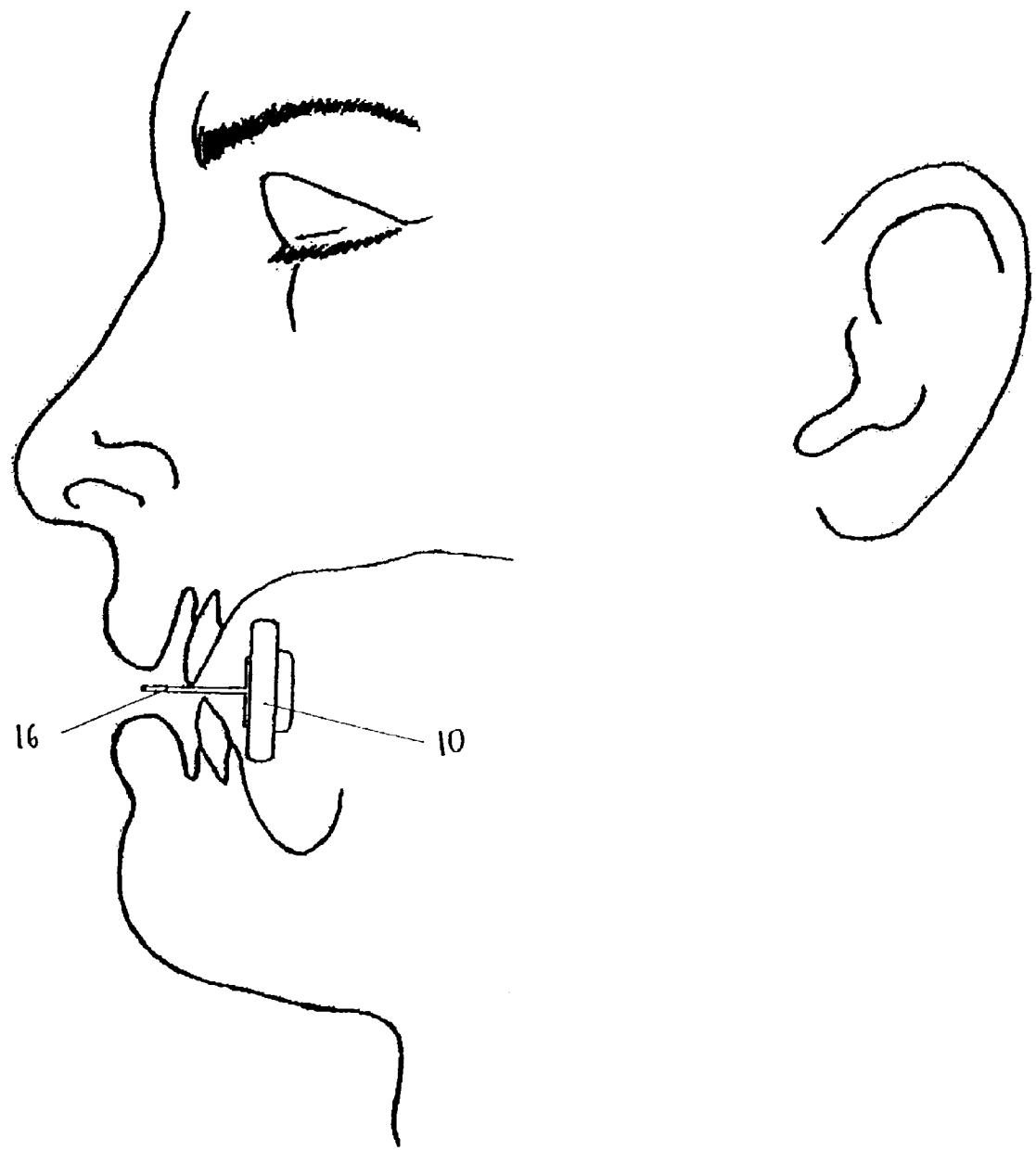
FIG. 3 is a drawing illustrating an application of the positioning system as used on a patient according to another embodiment of the present invention.

FIG. 3 is a drawing illustrating an application of the positioning system as used on a patient. The positioner used in FIG. 3 is a universal bite tab holder, although of course various other holders could have been chosen as an example. In the application of the positioning system as shown in FIG. 3, the appropriate holder 16 is attached to the receptor 10 by way of the adhesive, and the device is placed into the patient's mouth.

The holder 16 has a flat surface which is designed to stick to the receptor 10, and has a bite area for the patient to bite down on. The holder 16 is typically disposable as it is not used on different patients, but it may be re-positioned for different images, using the same adhesive, during the same patient examination.

In another embodiment (not shown), an interlocking device such as a plurality of pins is connected to an alignment arm for assisting in aligning the x-ray source.

The receptor may comprise a CCD or APS sensor, x-ray film, or any other dental system directly or indirectly sensitive to incident x-rays.

The adhesive itself may be made of tape, epoxy, hot melt, sealant, and the like, so long as it can support intra-oral sensor placement and has regulatory approval for food contact. In one embodiment, the adhesive may comprise a tape applied to the flat surface of the holder. The adhesive could be applied to the sheath by the user, or by the manufacturer, such as by the manufacturer of the holder.

In a preferred embodiment, an adhesive may be used that allows the holder to be removed and reapplied to the surface of the receptor; that is, the holder can be removably attached to the receptor. This might occur when a practitioner is using an electronic sensor and requires another x-ray image on the same patient, or when an alternate sensor position is deemed more comfortable or more useful, among other examples.

The holder may be any bitewing, bitetab, anterior, posterior, endodontic tab, aiming ring, or auxiliary positioning device, or another system used to position or align the receptor with an x-ray source. The holder may similarly be made of any biocompatible material capable of regulatory approval.

Figure 4:
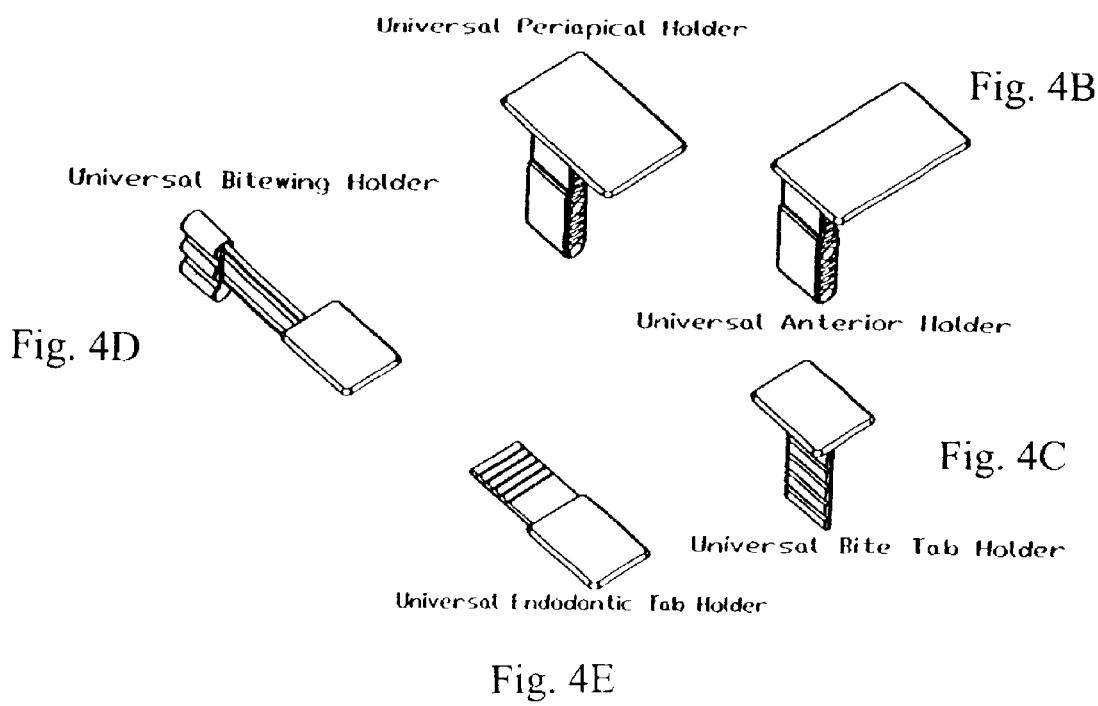
FIGS. 4A–E are illustrations of various holders used with the positioning system of the present invention.

FIGS. 4A–4E are illustrations of various holders that may be used with this invention. These types of holders are well known in the art, except that an adhesive is applied to them in accordance with the present invention. Of course, the invention is not limited to these types of holders, and many other types of holders may be used. By way of example, FIG. 4A shows a universal periapical holder; FIG. 4B shows a universal anterior holder; FIG. 4C shows a universal bitetab holder; FIG. 4D shows a universal bitewing holder; and FIG. 4E shows a universal endodontic tab holder. In a preferred embodiment, the holder is made out of a material, such as a thermoplastic resin, strong enough to repeatedly bond and release from the receptor. The preferred material may also withstand bite forces and the weight of the holder itself.

Figure 5:
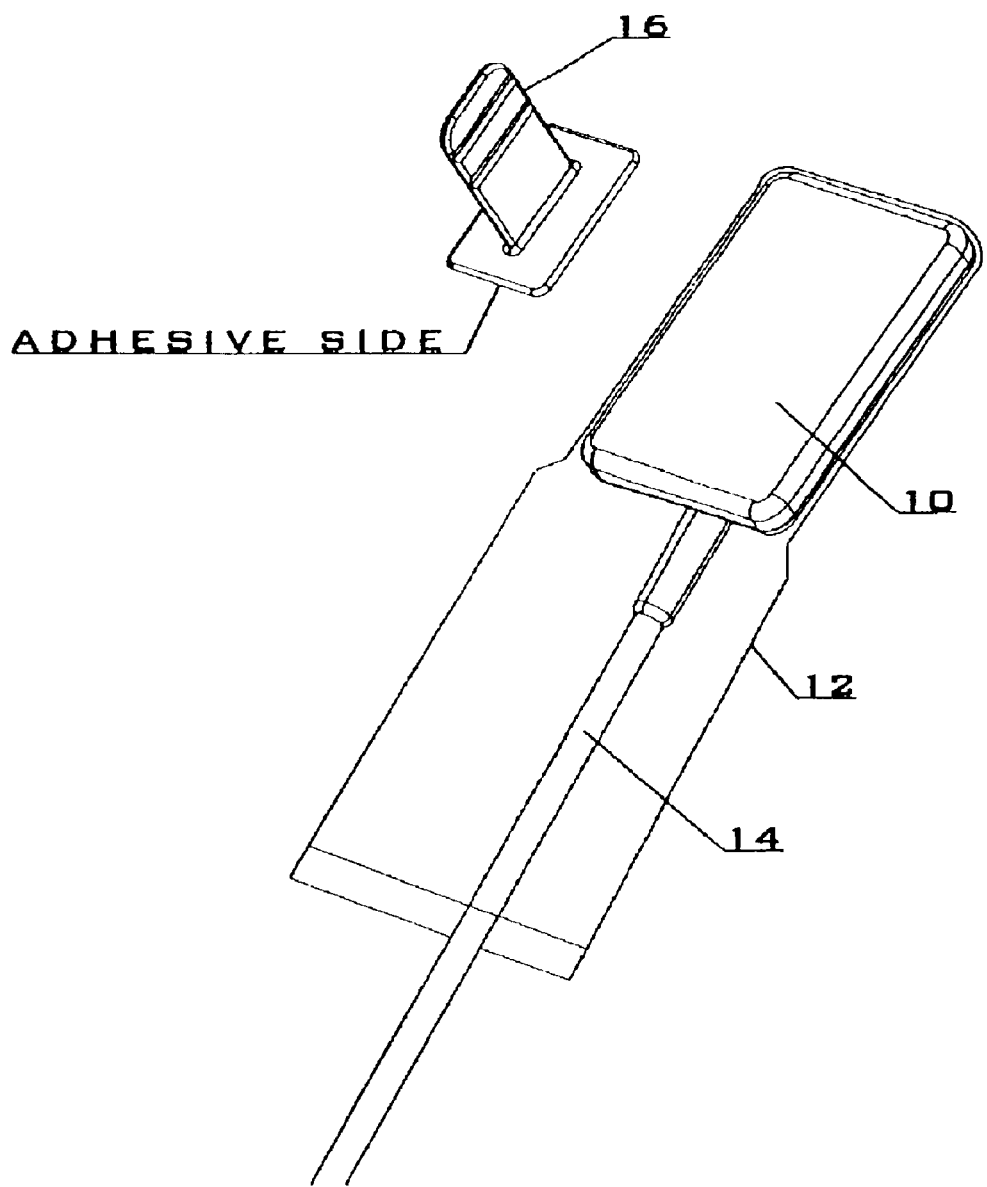
FIG. 5 is an illustration of the positioning system before being assembled and having a sheath, according to another embodiment of the invention.

In another embodiment, the sensor is covered with an anti-residue sheath which acts as a sterile infection barrier. FIG. 5 is an illustration of the positioning system before being assembled and having a sheath. An electronic sensor 10 and an anti-residue sheath 12 fitting snugly over the sensor 10 are shown in FIG. 5. A cable 14 protrudes from the sensor 10 to deliver the image to a processing unit (not shown). Also shown is a holder 16 on which a pressure sensitive adhesive is applied. The sensor 10 and sheath 12 are bonded with the adhesive to the holder 16 in a desired location. It is noted that although the adhesive is applied to the holder in the embodiment shown in FIG. 5, as is the preferred embodiment, the present invention is of course not limited to this embodiment, and various modifications may be imagined. For example, the adhesive could be applied to the sheath instead of to the holder.

Figure 6:
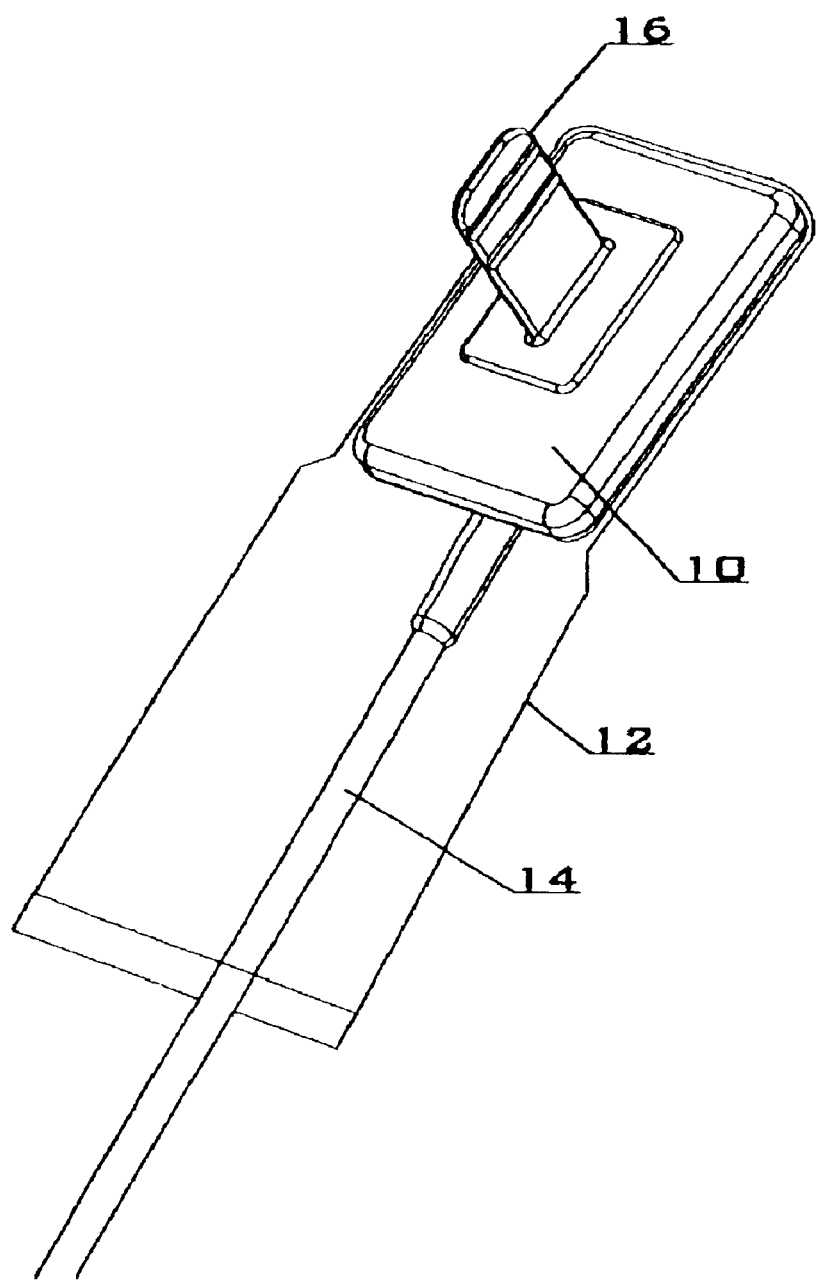
FIG. 6 is an illustration of the positioning system after being assembled and having a sheath, according to the embodiment shown in FIG. 5.

FIG. 6 is an illustration of the positioning system after being assembled and having a sheath, according to the embodiment shown in FIG. 5. FIG. 6 shows the receptor 10 covered snugly in the sheath 12, with the holder 16 affixed by way of the adhesive.

The sheath is made to form a tight fit with the receptor. The sheath may be made of a non-toxic radiolucent substance or barrier material such as paper, cotton, sponge, rubber, plastic, latex, nylon, or any other material permitted by a regulatory body for invasive use. In a preferred embodiment, the sheath is a thermoplastic resin which is transparent, disposable, infection resistant, resilient, bio-compatible, and FDA-approved.

Of course, a sheath may not be required when the dental positioning system is used in conjunction with a disposable receptor such as an x-ray film packet. Also, a sheath may not be required if the receptor is sterilized, among other examples.

In the case of an electronic sensor, the sheath may encapsulate the entire device and cable, thereby providing a more cost-efficient anti-infection barrier. A sheath with a slimmed profile would prevent the sensor from slipping out. Preferably, the sheath should be resistant to any tears that might occur in the sheath when the holder is removed. Also, the sheath can not only be used repeatedly in the same patient, but it is also resistant to residue buildup from the chosen adhesive. In a preferred embodiment, an adhesive may be used that allows the holder to be removed and reapplied to the surface of the sheath.

The sheath and holder may be pre-assembled as one component held together by an adhesive. With this arrangement, the dental practitioner would not be required to assemble the package prior to clinical application. Alternatively, the holders could be dispensed on a strip with adhesive backing.

While the invention has been particularly shown and described with respect to preferred embodiments thereof, it will be understood by those skilled in the art that changes in form and details may be made therein without departing from the scope and spirit of the invention.

Having described the invention, what is claimed as new and secured by Letters Patent is:

1. A positioning system for dental x-ray examinations, comprising:
   an electronic image sensor;
   a sheath covering the electronic image sensor; and
   a holder removably bonded to the sheath by a pressure sensitive adhesive upon application of the holder to the sheath just prior to positioning the holder and the electronic sensor;
   wherein the pressure sensitive adhesive enables the holder to be adjustably positioned on the sheath in a manner that provides optimal coverage of a patient's dental anatomy by the electronic image sensor.

2. The positioning system as set fort in claim 1, wherein the electronic image sensor comprises a charge-coupled device.

3. The positioning system as set forth in claim 1, wherein the electronic image sensor comprises a CMOS active pixel sensor array.

4. The positioning system as set forth in claim 1, wherein the holder is bonded to the sheath at any point along a surface of the electronic image sensor.

5. The positioning system as set forth in claim 1, wherein the sheath is a material selected from the group consisting of paper, cotton, sponge, rubber, plastic, latex, and nylon.

6. The positioning system as set forth in claim 1, wherein the adhesive is selected from the group consisting of tape, epoxy, hot melt, and sealant.

7. A method for positioning an electronic dental image sensor, comprising the steps of:
   placing the electronic sensor in a sheath;
   affixing a holder having a pressure sensitive adhesive to the sheath to create a removable bond between the holder and the sheath just prior to positioning the holder and the electronic sensor;
   positioning the holder and the electronic sensor within the mouth of a patient;
   capturing at least one dental image; and
   removing the holder from the sheath following the capture of the at least one dental image,
   wherein the pressure sensitive adhesive enables the holder to be adjustably positioned on the sheath in a manner that provides optimal coverage of the patient's dental anatomy by the electronic sensor.

8. The method as set forth in claim 7, wherein the holder is bonded to the sheath at any point along a surface of the electronic image sensor.

9. The method as set forth in claim 7, wherein the sheath is a material selected from the group consisting of paper, cotton, sponge, rubber, plastic, latex, and nylon.

10. The method as set forth in claim 7, wherein the adhesive is selected from the group consisting of tape, epoxy, hot melt, and sealant.

11. A positioning system for dental x-ray examinations, comprising:
    an electronic image sensor; and
    a holder removably bonded to the electronic image sensor by a pressure sensitive adhesive upon a application of the holder to the electronic image sensor just prior to positioning the holder and the electronic sensor, wherein the pressure sensitive adhesive enables the holder to be adjustably positioned on the electronic image sensor in a manner that provides optimal coverage of a patient's dental anatomy by the electronic image sensor.

12. The dental positioning system as set forth in claim 11, wherein the electronic image sensor comprises a CMOS active pixel sensor array.

13. The dental positioning system as set forth in claim 11, wherein the electronic image sensor comprises a charge-coupled device.

14. The dental positioning system as set forth in claim 11, wherein the adhesive is selected from the group consisting of tape, epoxy, hot melt, and sealant.

15. A method for enabling a dental practitioner to position an electronic dental image sensor, comprising steps of:

affixing a holder having a pressure sensitive adhesive to the electronic image sensor to create a removable bond between the holder and the electronic image sensor just prior to positioning the holder and the electronic image sensor;

positioning the holder and the electronic image sensor within the mouth of a patient;

capturing at least one dental image; and removing the holder from the electronic image sensor following the capture of at lease one dental image, wherein the pressure sensitive adhesive enables the holder to be adjustably positioned on the electronic image sensor in a manner that provides optimal coverage of the patient's dental anatomy by the electronic sensor.

16. The method as set forth in claim 15, wherein the electronic image sensor comprises a CMOS active pixel sensor array.

17. The method as set forth in claim 15, wherein the electronic image sensor comprises a charge-coupled device.

18. The method as set forth in claim 15, wherein the adhesive is selected from the group consisting of tape, epoxy, hot melt, and sealant.

19. A positioning system for dental x-ray examinations, comprising:

an electronic image sensor;

a sheath covering the electronic image sensor; and a holder removably bonded to the sheath by a pressure sensitive adhesive upon application of the holder to the sheath just prior to positioning the holder and the electronic sensor;

wherein the pressure sensitive adhesive enables the holder to be adjustably positioned on the sheath in a manner that optimizes a patient's comfort when the electronic image sensor is placed in the patient's mouth.

20. A method for enabling a dental practitioner to position an electronic dental image sensor, comprising the steps of:

placing the electronic sensor in a sheath;

affixing a holder having a pressure sensitive adhesive to the sheath to create a removable bond between the holder and the sheath just prior to positioning the holder and the electronic sensor;

positioning the holder and the electronic sensor within the mouth of a patient;

capturing at least one dental image; and removing the holder from the sheath following the capture of the at least one dental image;

wherein the pressure sensitive adhesive enables the holder to be adjustably positioned on the sheath in a manner that optimizes the patient's comfort when the electronic sensor is placed in the patient's mouth.

21. A positioning system for dental x-ray examinations, comprising:

an electronic image sensor; and a holder removably bonded to the electronic image sensor by a pressure sensitive adhesive upon a application of the holder to the electronic image sensor just prior to positioning the holder and the electronic sensor, wherein the pressure sensitive adhesive enables the holder to be adjustably positioned on the electronic image sensor in the patient's comfort when the manner that optimizes a electronic sensor is placed in the patient's mouth.

22. A method for enabling a dental practitioner to position an electronic dental image sensor, comprising steps of:

affixing a holder having a pressure sensitive adhesive to the electronic image sensor to create a removable bond between the holder and the electronic image sensor just prior to positioning the holder and the electronic image sensor;

positioning the holder and the electronic image sensor within the mouth of a patient;

capturing at least one dental image; and removing the holder from the electronic image sensor following the capture of at lease one dental image, wherein the pressure sensitive adhesive enables the holder to be adjustably positioned on the electronic image sensor in a manner that optimizes the patient's comfort when the electronic sensor is placed in the patient's mouth.

* * * * *